United States Patent [19]
Quame

[11] 3,947,251
[45] Mar. 30, 1976

[54] LABORATORY CONTAINER

[76] Inventor: Babington A. Quame, 331 E. 29th St., New York, N.Y. 10016

[22] Filed: Oct. 16, 1974

[21] Appl. No.: 515,355

Related U.S. Application Data

[62] Division of Ser. No. 294,849, Oct. 4, 1972, Pat. No. 3,843,323.

[52] U.S. Cl.................... 23/259; 23/292; 73/421 R
[51] Int. Cl.².......................................... B01L 3/00
[58] Field of Search................. 23/259, 292, 253 R; 73/421 R

[56] References Cited
UNITED STATES PATENTS

| | | | |
|---|---|---|---|
| 2,859,620 | 11/1958 | Rhodes et al. | 73/421 R |
| 3,545,932 | 12/1970 | Gilford | 23/292 X |
| 3,774,455 | 11/1973 | Seidler et al. | 23/259 X |
| 3,843,323 | 10/1974 | Quame | 23/253 R X |

*Primary Examiner*—Morris O. Wolk
*Assistant Examiner*—Arnold Turk
*Attorney, Agent, or Firm*—Steinberg & Blake

[57] ABSTRACT

A laboratory container having an open top closed by a funnel in the container to direct liquid into the same with the funnel carrying a structure to prevent liquid from spilling out through the funnel when the container and funnel are inverted. A valve communicates with the interior of the container to discharge liquid therefrom when the container is inverted.

3 Claims, 5 Drawing Figures

LABORATORY CONTAINER

CROSS REFERENCE TO RELATED APPLICATION

This application is a divisional of copending application Ser. No. 294,849 filed Oct. 4, 1972, now U.S. Pat. No. 3,843,323 and entitled, "Method and Apparatus for Sample Evaluation".

BACKGROUND OF THE INVENTION

The present invention relates to containers for sample evaluation.

In particular, the present invention relates to containers for evaluating urine samples to determine whether or not any given urine sample contains a drug such as narcotic analgesics, amphetamines, and addictive sedatives.

Although the basic chemistry required for such sampling operations is known, the manipulations involved are very time consuming so that a considerable amount of labor, time, and costs are required to carry out the sampling procedures in connection with a large number of urine samples. As a result it is not uncommon to encounter large backlogs of samples which require testing at any given facility where such sampling is carried out. In addition, the costs involved are very high, so that considerable difficulty is encountered in obtaining funding to carry out the above procedures to the extent required by the widespread drug problem so common in large metropolises.

An additional drawback encountered with conventional procedures of the above type is that they must be carried out by relatively skilled personnel so that the labor costs are extremely high.

SUMMARY OF THE INVENTION

It is accordingly a primary object of the present invention to provide a container which will avoid the above drawbacks.

In particular, it is an object of the present invention to provide containers for liquids such as urine samples to enable large numbers of samples to be handled in an extremely short time with a relatively simple apparatus of relatively small dimensions which can be operated by relatively unskilled personnel.

According to the invention the container has an open top closed by a funnel means which directs liquid into the interior of the container. The funnel means carries a means for preventing the contents of the container from spilling out through the funnel means when the container and funnel means therewith are inverted. A valve means is carried by the container and communicates with the interior thereof for discharging liquid from the interior of the container when the latter is inverted.

BRIEF DESCRIPTION OF DRAWINGS

The invention is illustrated by way of example in the accompanying drawings which form part of this application and in which.

DESCRIPTION OF A PREFERRED EMBODIMENT

Figure 2:
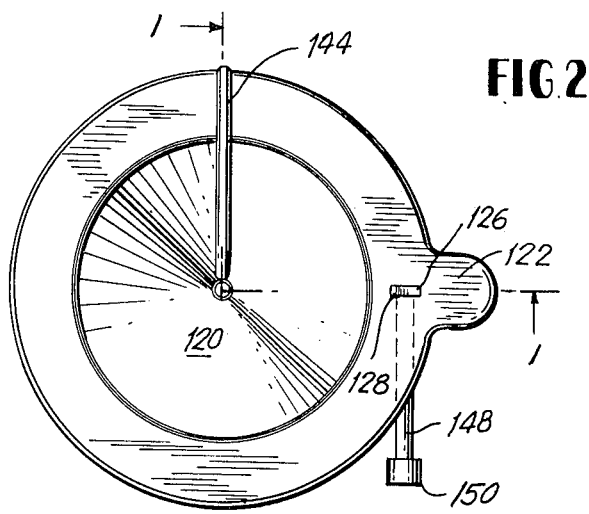
FIG. 2 is a top plan view of the container of FIG. 1.
Figure 1:
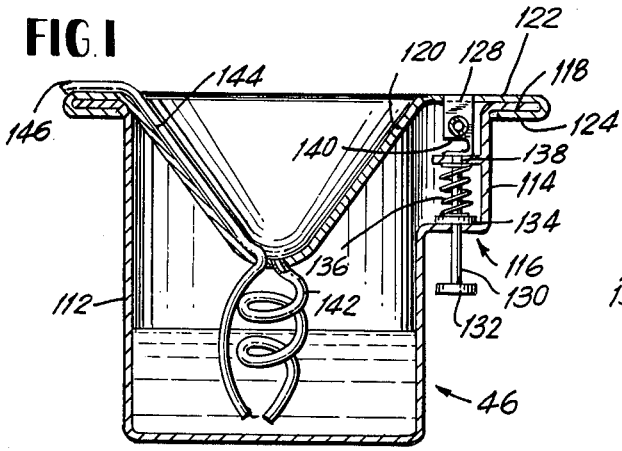
FIG. 1 is a sectional elevation, taken along lines 1—1 of FIG. 2 in the direction of the arrows, showing the details of a container of the invention.
Figure 3:
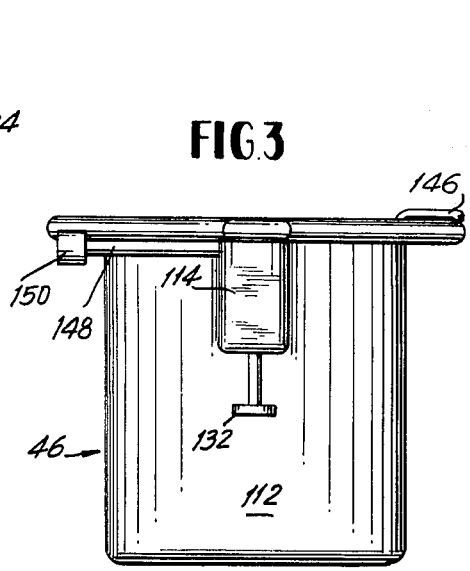
FIG. 3 is an elevation of the container of FIG. 1 as seen from the right of FIG. 1.

The details of a container means 46 of the invention are illustrated in FIGS. 1–5.

Thus, container means 46 includes an outer container 112 which is adapted to receive a portion of a urine sample. This container 112 may have a cylindrical configuration except that it has a hollow projecting portion 114 at one side for accommodating a valve means 116, and the openings of a conveyer have a configuration which is circular except for a projection to receive the part 114 of container 112. Thus, the configuration of a conveyer opening matches the cross section of the container means 46 at a location just beneath the top flange 118 of the container 112.

Each container 112 carries a funnel means 120 made of any suitable plastic, and having a top flange 122 which extends around the flange 118 with part of the flange 122 having a lower portion 124 which snaps beneath the flange 118 so that the funnel means 120 is fluid-tightly carried by the flange 118 and projects into the interior of the container 112. Part of the flange 122 is formed with a slot 126 which receives the top end of a slidable valve member 128.

The valve means 116 includes in addition to the valve plate 128 an elongated pin 130 which has at one end a head 132 adapted to be pressed upon by an actuating roller, as described in greater detail below. The pin 130 extends through a suitable opening formed in the lower wall of the projecting portion 114, and next to this lower wall, as viewed in FIG. 1, the pin 130 carries a flange 134. A coil spring 136 surrounds the pin 130 above the flange 134, as viewed in FIG. 1 and presses downwardly against the flange 134, with the top of the spring 136 pressing against an interior horizontal projection 138 of the container 112 at the hollow extension 114 thereof. The top of the pin 130 is fixed to the slidable valve plate 128 which is formed with an elongated notch 140 for a purpose referred to below.

The funnel 120 of container means 46 carries at its bottom end a hollow spiral tube 142 which may be made of any suitable plastic. Thus, when a urine sample is poured into a container portion 112, the sample will flow through the spiral tube 142 into the interior of the container 112 so that when the latter is inverted the urine will not spill out of the container means 46 but will be retained in the container portion 112 by the inner surface of the funnel means 120. In addition, container means 46 includes an air tube 144 which extends along the funnel means 120 in the manner shown in FIG. 1, fluid-tightly through the latter into the interior of the container 112. Tube 144 has an outer open end 146 communicating freely with the outer atmosphere. As a result, when the container 46 is inverted air can flow freely into the interior of the container while the liquid therein flows down to assume the condition shown in FIG. 4.

Figure 4:
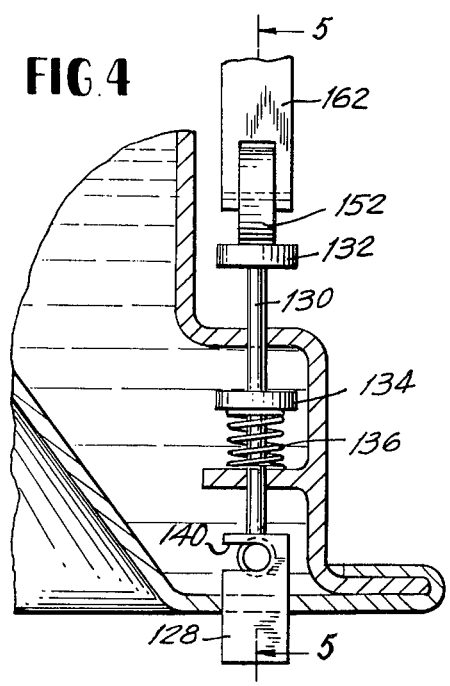
FIG. 4 is a fragmentary sectional elevation on an enlarged scale as compared to the remaining FIGS. and showing how a valve-actuating means operates a valve of the container.
Figure 5:
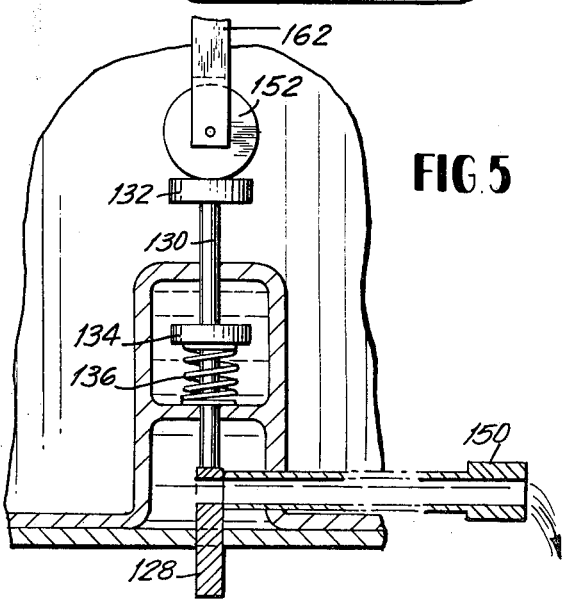
FIG. 5 is a fragmentary sectional elevation taken along line 5—5 of FIG. 4 in the direction of the arrows.

Projection 114 of the container 46 fixedly carries an elongated discharge tube 148 having an inner end, in the hollow interior of projection 114 which is slidably engaged by the valve plate 128 so that the inner end of the discharge tube 148 is normally closed. Plate 128 is formed with a notch 140 (FIG. 4). The outer end 150 is situated at the exterior of the container and if desired may carry a plug of cotton or other filtering material.

As each container means 46 is advanced by an unillustrated conveyer to a receiving station, the several container means are inverted, since they are initially carried by an upper run of an endless conveyer and are inverted at the lower run thereof when reaching roller 152. Arm 162 rotatably supports the valve-actuating roller 152. The location of the roller 152 is such that when each container 46 reaches the roller, the head 132 will move beneath the roller 152 which is maintained at the elevation shown in FIG. 4, and thus the stem 130 will be depressed in opposition to the spring 136, thus locating the notch 140 in alignment with the inner open end of the discharge tube 148. As a result the liquid will discharge through the discharge tube 148.

Thus, in utilizing the apparatus of the invention as described above, a series of clean, dry containers 46 are placed in openings of an elongated plate of a conveyer. Then several urine samples are respectively poured into the several containers 46 through the funnel means 120 thereof, and of course suitable identifying indicia are maintained with the samples and with the containers as the samples are treated, so that, for example, spots on the chromatographic plates will be identified with specific samples initially placed in each row or series of containers 46 carried by a conveyer plate. Each container 46 may have in its interior two liquid phases one of which is heavier and situated beneath the other. As a result when the several containers 46 are inverted to assume the positions shown in FIGS. 4 and 5, it is the heavier phase which is located at the bottom directly next to the valve means 116, and thus when the several valve means are opened by the roller 152, it is only the heavier phase which is discharged, the container moving beyond roller 152 before the lighter liquid phase can be discharged.

What is claimed is:

1. For use in the testing of liquid samples, a container having an open top, funnel means closing said open top of said container for directing liquid into the interior of the latter, means carried by said funnel means for preventing the contents of the container from spilling out through said funnel means when said container and funnel means therewith are inverted, valve means carried by said container and communicating with the interior thereof for discharging liquid from the interior of the container when the latter is inverted and means for admitting air into the interior of the container beneath the funnel means.

2. The combination of claim 1 and wherein said valve means is located adjacent the top of the container so that when the latter is inverted said valve means will discharge liquid from the lowermost portion of the inverted container.

3. The combination of claim 2 where said means for admitting air comprises a tubular means communicating with the exterior of the container and with the interior of the container beneath said funnel means.

* * * * *